US012616721B2

(12) United States Patent
Nishida et al.

(10) Patent No.: US 12,616,721 B2
(45) Date of Patent: May 5, 2026

(54) STRATIFIED SQUAMOUS EPITHELIAL CELL NORMAL DIFFERENTIATION AND MATURATION PROMOTING AGENT, EPITHELIAL DISEASE THERAPEUTIC AGENT, AND STRATIFIED SQUAMOUS EPITHELIAL CELL NORMAL DIFFERENTIATION AND MATURATION PROMOTING METHOD

(71) Applicants: OSAKA UNIVERSITY, Osaka (JP); ROHTO PHARMACEUTICAL CO., LTD., Osaka (JP)

(72) Inventors: Kohji Nishida, Osaka (JP); Ryuhei Hayashi, Osaka (JP); Shun Shibata, Osaka (JP); Toru Okubo, Osaka (JP); Yoichi Honma, Osaka (JP)

(73) Assignees: OSAKA UNIVERSITY, Osaka (JP); ROHTO PHARMACEUTICAL CO., LTD., Osaka (JP)

( * ) Notice: Subject to any disclaimer, the term of this patent is extended or adjusted under 35 U.S.C. 154(b) by 1291 days.

(21) Appl. No.: 16/961,354

(22) PCT Filed: Jan. 11, 2019

(86) PCT No.: PCT/JP2019/000751
§ 371 (c)(1),
(2) Date: Sep. 21, 2020

(87) PCT Pub. No.: WO2019/139137
PCT Pub. Date: Jul. 18, 2019

(65) Prior Publication Data
US 2021/0046122 A1 Feb. 18, 2021

(30) Foreign Application Priority Data
Jan. 12, 2018 (JP) ................................. 2018-003518

(51) Int. Cl.
*A61K 35/28* (2015.01)
*A61P 27/02* (2006.01)

(52) U.S. Cl.
CPC .............. *A61K 35/28* (2013.01); *A61P 27/02* (2018.01)

(58) Field of Classification Search
CPC . A61K 35/28; A61P 27/02; A61P 1/02; A61P 17/00
See application file for complete search history.

(56) References Cited

U.S. PATENT DOCUMENTS

| | | | |
|---|---|---|---|
| 8,034,329 | B2 | 10/2011 | Colter |
| 10,238,692 | B2 | 3/2019 | Yang et al. |
| 2009/0092653 | A1 | 4/2009 | Colter et al. |
| 2011/0217385 | A1 | 9/2011 | Lian et al. |
| 2011/0262393 | A1 | 10/2011 | Yang et al. |
| 2013/0195991 | A1 | 8/2013 | Ueda et al. |
| 2018/0325946 | A1 | 11/2018 | Ueda et al. |
| 2019/0015452 | A1 | 1/2019 | Nishida et al. |

FOREIGN PATENT DOCUMENTS

| | | |
|---|---|---|
| CN | 106265744 | 1/2017 |
| CN | 107412266 | 12/2017 |
| JP | 2007-528703 | 10/2007 |
| JP | 2010-538681 | 12/2010 |
| JP | 2010-540662 | 12/2010 |
| JP | 2010538681 A * | 12/2010 |
| JP | 2012-508733 | 4/2012 |
| JP | 2012-157263 | 8/2012 |
| WO | 2005/001077 | 1/2005 |
| WO | 2011/118795 | 9/2011 |
| WO | 2012/166932 | 12/2012 |
| WO | 2014/022685 | 2/2014 |
| WO | 2017/022628 | 2/2017 |

(Continued)

OTHER PUBLICATIONS

WO-2017022809-A1, Translation, 13 pages. <https://worldwide. espacenet.com/patent/search/family/057944207/publication/ WO2017022809A1?q=pn%3DWO2017022809A1>. (Year: 2017).*
First Office Action issued Oct. 21, 2022 in corresponding Chinese Patent Application No. 201980007621.3, with English language translation, 12 pages.
Notice of Reasons for Refusal issued Nov. 29, 2022 in corresponding Japanese Patent Application No. 2019-564765, with English language translation, 8 pages.
Xin Dong et al., "Application and research progress of bone marrow mesenchymal stem cells in corneal injury repair", Int Eye Sci, 2017, vol. 17, No. 11, pp. 2060-2064, with the English Abstract, 5 pages.
Yihan Li et al., "Poly(ethylene glycol)-modified silk fibroin membrane as a carrier for limbal epithelial stem cell transplantation in a rabbit LSCD model", Stem Cell Research & Therapy, 2017, vol. 8, No. 256, pp. 1-19.

(Continued)

*Primary Examiner* — Aaron J Kosar
*Assistant Examiner* — Jennifer Lynn Cain
(74) *Attorney, Agent, or Firm* — Wenderoth, Lind & Ponack, L.L.P.

(57) ABSTRACT

The present invention addresses the problem of providing a novel therapeutic agent that is effective against diseases involving stratified squamous epithelial cells such as dry eye syndrome. The present invention is an agent for promoting normal differentiation/maturation of stratified squamous epithelial cells, which comprises a secretion of mesenchymal stem cells. It is preferable that the secretions not include animal serum, that the mesenchymal stem cells be adipose-derived mesenchymal stem cells, umbilical cord-derived mesenchymal stem cells, or bone marrow-derived mesenchymal stem cells, and that the stratified squamous epithelial cells be at least one selected from the group consisting of corneal epithelial cells, conjunctival epithelial cells, epidermal keratinocytes, oral epithelial cells, epiglottic epithelial cells, esophageal epithelial cells, vaginal epithelial cells, vocal fold epithelial cells, nasal epithelial cells, and nasal vestibular epithelial cells.

5 Claims, 5 Drawing Sheets

(56) References Cited

FOREIGN PATENT DOCUMENTS

| WO | 2017/022809 | 2/2017 | | |
| WO | WO-2017022809 A1 * | 2/2017 | ............. | A61K 35/12 |

OTHER PUBLICATIONS

Pittenger et.al., "Multilineage Potential of Adult Human Mesenchymal Stem Cells", Science, Apr. 1999, vol. 284, pp. 143-147.

Beyazyildiz et al., "Efficacy of Topical Mesenchymal Stem Cell Therapy in the Treatment of Experimental Dry Eye Syndrome Model", Stem Cells Int., 2014; vol. 2014, Article ID 250230, pp. 1-9.

Tomasoni et al., "Transfer of growth factor receptor mRNA via exosomes unravels the regenerative effect of mesenchymal stem cells", Stem Cells and Development, 2013, vol. 22, No. 5, pp. 772-780.

International Search Report issued Mar. 12, 2019 in International (PCT) Application No. PCT/JP2019/000751.

Extended European Search Report issued May 10, 2021 in corresponding European Patent Application No. 19738369.8.

Shimojima et al., "Conditioned Medium from the Stem Cells of Human Exfoliated Deciduous Teeth Ameliorates Experimental Autoimmune Encephalomyelitis", Journal of Immunology, 2016, vol. 196, No. 6, pp. 4164-4171, 9 pages.

Tanifuji-Terai et al., "Expression of Keratin 12 and Maturation of Corneal Epithelium during Development and Postnatal Growth", Investigative Ophthalmology & Visual Science, 2006, vol. 47, No. 2, pp. 545-551, 7 pages.

* cited by examiner

1

STRATIFIED SQUAMOUS EPITHELIAL CELL NORMAL DIFFERENTIATION AND MATURATION PROMOTING AGENT, EPITHELIAL DISEASE THERAPEUTIC AGENT, AND STRATIFIED SQUAMOUS EPITHELIAL CELL NORMAL DIFFERENTIATION AND MATURATION PROMOTING METHOD

TECHNICAL FIELD

The present invention relates to an agent for promoting normal differentiation/maturation of stratified squamous epithelial cells, an epithelial disease therapeutic agent and a method for promoting normal differentiation/maturation of stratified squamous epithelial cells.

BACKGROUND ART

The ocular surface plays an important role in protecting the eye from outside infection sources. A major disease of the ocular surface, dry eye, is a chronic disease of tear fluid, corneal epithelium and conjunctival epithelium, caused by qualitative or quantitative abnormity of tear fluid and causes a sense of discomfort in the eye and visual abnormality. Of the dry-eye diseases, serious dry eye such as Sjogren's syndrome significantly decreases quality of life (QOL) and sometimes causes blindness. Note that, the number of Sjogren's syndrome patients in Japan is reported to be 70,000, and probably, 200,000 or more if the number of potential patients are included.

Treatments for dry eye conventionally known include a method of placing an eye-drop using artificial tear; a method of using a moisture aid which consists of panels to be provided to both sides of a pair of glasses to prevent evaporation of tear; a punctual occlusion method, which is a method of closing a tear discharge port, punctum, to keep tear fluid in the conjunctival sac; a method of applying hyaluronic acid to keep moisture, and a method of promoting secretion of mucin and a moisture content by administering a drug. However, any one of the methods is unsatisfactory.

In the meantime, development of medicines using cells and cell-culture supernatant have been broadly made. For instance, mesenchymal stem cells are precursor cells having pluripotency, which were, for the first time, isolated by Friedenstein from the bone marrow (see, Non Patent Document 1). It has been found that the mesenchymal stem cells are present in a wide variety of tissues such as bone marrow, umbilical cord and adipose tissues, and involved in repair of various tissues and have immunosuppressive effect. Transplantation of mesenchymal stem cells is expected as a novel therapy for various types of intractable diseases (see, Patent Documents 1 and 2). In addition, e.g., a method of using a pharmaceutical composition containing a culture supernatant of mesenchymal stem cells for repairing damaged sites of a target tissue (see, Patent Documents 3 and 4) and a method of using a pharmaceutical composition containing a culture supernatant of mesenchymal stem cells for treating a secondary fibromyalgia caused by diseases or damages (see, Patent Document 5) are also known.

Non Patent Document 2 reports that stability of tear fluid can be improved by instilling mesenchymal stem cells themselves in a rat model having dry eye, which is induced by placing a drop of benzalkonium chloride, and discloses that, in this model, mesenchymal stem cells instilled infiltrate into the meibomian glands and conjunctival epithelium, and contribute to improvement of tear fluid stability.

PRIOR ART DOCUMENTS

Patent Document

Patent Document 1: JP 2012-157263 A
Patent Document 2: JP 2012-508733 A
Patent Document 3: International Publication No. WO2011/118795
Patent Document 4: JP 2010-540662 A
Patent Document 5: JP 2007-528703 A

Non Patent Document

Non Patent Document 1: Pittenger F. M. et. al., Science, 1999, 284, pp. 143-147
Non Patent Document 2: Beyazyildiz E. et. al. Stem Cells Int. 2014; vol. 2014: 250230

SUMMARY OF INVENTION

Technical Problem

In the circumstance, it has been desired to develop a therapeutic agent having a higher effect than conventional ones on diseases such as dry eye, in which the stratified squamous epithelial cells are involved, particularly, a therapeutic agent based on a new mechanism of action. Then, an object of the present invention is to provide a novel therapeutic agent effective for a disease such as dry eye, in which stratified squamous epithelial cells are involved.

Solution to Problem

The present inventors conducted various studies with a view to attaining the object. As a result, they found that normal differentiation/maturation and formation of tight junction between cells can be promoted by adding a secretion from mesenchymal stem cells to corneal epithelial cells, thereby improving barrier function. Based on the finding, the present invention was accomplished. The present invention is summarized as follows.

[1] An agent for promoting normal differentiation/maturation of stratified squamous epithelial cells, which comprises a secretion from mesenchymal stem cells.

[2] The normal differentiation/maturation-promoting agent according to [1], wherein the secretion does not include animal serum.

[3] The normal differentiation/maturation-promoting agent according to [1] or [2], wherein the mesenchymal stem cells are adipose-derived mesenchymal stem cells, umbilical cord-derived mesenchymal stem cells or bone marrow-derived mesenchymal stem cells.

[4] The normal differentiation/maturation-promoting agent according to any one of [1] to [3], wherein the stratified squamous epithelial cells comprise at least one type of cells selected from the group consisting of corneal epithelial cells, conjunctival epithelial cells, epidermal keratinocytes, oral epithelial cells, epiglottis epithelial cells, esophageal epithelial cells, vaginal epithelial cells, vocal cord fold epithelial cells, nasal epithelial cells and nasal vestibular epithelial cells.

[5] An epithelial disease therapeutic agent comprising the normal differentiation/maturation-promoting agent according to any one of [1] to [4].

[6] The epithelial disease therapeutic agent according to [5], wherein the epithelial disease is a disease involving a tissue having the stratified squamous epithelial cells.

[7] The epithelial disease therapeutic agent according to [6], wherein the epithelial disease is a corneal disease, a conjunctival disease, an oral disease or an epidermal disease.

[8] The epithelial disease therapeutic agent according to [7], wherein the epithelial disease is dry eye, pterygium, scar, EB viral keratitis, corneal epithelial stem cell deficiency, Sjogren's syndrome or scleroderma.

[9] A method for promoting normal differentiation/maturation of stratified squamous epithelial cells, comprising using a secretion from mesenchymal stem cells.

Advantageous Effects of Invention

According to the present invention, normal differentiation/maturation of cells and formation of tight junction between cells can be promoted by adding a normal differentiation/maturation-promoting agent comprising a secretion from mesenchymal stem cells to stratified squamous epithelial cells, i.e., corneal epithelial cells, thereby improving barrier function. The therapeutic agent containing a normal differentiation/maturation-promoting agent is effective for an epithelial disease of a tissue having stratified squamous epithelial cells such as eye, for example, dry eye.

DESCRIPTION OF EMBODIMENTS

Figure 1:
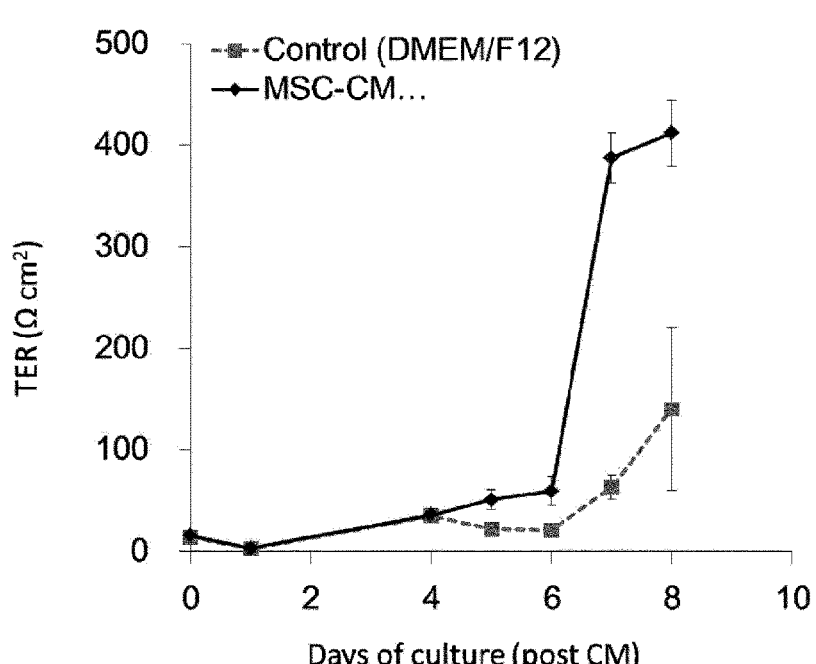
FIG. 1 is a graph showing a barrier function promotion effect of a secretion from mesenchymal stem cells (MSC-CM) on corneal epithelial cells.

Now, the present invention will be more specifically described.

<Agent for Promoting Normal Differentiation/Maturation of Stratified Squamous Epithelial Cells>

The agent for promoting normal differentiation/maturation of stratified squamous epithelial cells of the present invention comprises a secretion from mesenchymal stem cells. According to the normal differentiation/maturation-promoting agent of the present invention, it is possible to promote normal differentiation/maturation of stratified squamous epithelial cells such as corneal epithelial cells and promote formation of tight junctions between cells, thereby improving barrier function of the tissue.

[Stratified Squamous Epithelial Cells]

The epithelium tissues are classified into groups based on the shape of epithelial cells lined up, such as flat, cubic and cylindrical shapes, and also classified into a single-layer and a multi-layer based on whether the cells are arranged in a single layer or piled up vertically in multiple stages. Examples of single-layer squamous epithelium include epithelium lining a blood vessel and a lymph vessel; whereas examples of single-layer columnar epithelium include intestinal epithelium lining the luminal surface of the intestine. The stratified squamous epithelium on which the normal differentiation/maturation-promoting agent of the present invention produces a differentiation/maturation-inducing effect is the epithelium covering the surfaces of, e.g., eyes and skin and known to be resistant against mechanical stimuli such as friction.

In the present invention, the stratified squamous epithelial cells are not only the cells of eyes and skin as mentioned above but also the cells of epithelium tissues such as oral cavity, epiglottis (posterior part), esophagus, vagina, vocal folds, nose vestibule and nasal cavity. Specific examples thereof include corneal epithelial cells, conjunctival epithelial cells, epidermal keratinocytes, oral epithelial cells, epiglottis epithelial cells, esophageal epithelial cells, vaginal epithelial cells, vocal cord fold epithelial cells, nasal epithelial cells and nasal vestibular epithelial cells. Of them, in consideration that the effect of the secretion from mesenchymal stem cells to promote normal differentiation/maturation and the effect of forming tight junction between cells are significant, corneal epithelial cells, conjunctival epithelial cells, oral epithelial cells and epidermal keratinocytes are preferable.

The "normal differentiation/maturation" in the normal differentiation/maturation-promoting agent of the present invention refers to normal differentiation/maturation of stratified squamous epithelial cells. If the stratified squamous epithelial cells are normally differentiated, they are formed into morphologically flat and big cells and formation of tight junction between the cells is promoted. In view of gene expression, if the stratified squamous epithelial cells are normally differentiated, expressions of, e.g., KRT12, KRT13, KRT14, CLDN1, TJP1 and CDH1 increase More specifically, the agent for promoting normal differentiation/maturation of stratified squamous epithelial cells of the present invention can normally differentiate stratified squamous epithelial cells, induce expression of various proteins, promote formation of tight junction between cells and finally form a tissue having excellent barrier function. Note that, normal differentiation of stratified squamous epithelial cells finally into matured cells having a function, in other words, reaching a differentiation final stage, is called maturation. As described, since normal differentiation and maturation are closely related events, the normal differentiation/maturation-promoting agent of the present invention can be referred to also as a normal differentiation promoting agent.

Components contained in the agent for promoting normal differentiation/maturation of stratified squamous epithelial cells of the present invention will be described, below. The agent for promoting normal differentiation/maturation of stratified squamous epithelial cells of the present invention contains, in addition to an essential component, i.e., a secretion from mesenchymal stem cells, other components as long as they do not undermine the effect of the present invention.

[Secretion from Mesenchymal Stem Cells]

(Mesenchymal Stem Cells)

In the present invention, the mesenchymal stem cells refer to cells, which have differentiation potential into any of cells belonging to the mesenchymal cells, such as bone cells, cardiomyocytes, chondrocytes, tendon cells and adipose cells, and which can proliferate while maintaining the differentiation potential. Example thereof include mesenchymal stem cells derived from adipose, umbilical cord, bone marrow, blood, periosteum, dermis, placenta, amniotic membrane, chorion, decidua, muscle, endometrium, dermis, tooth follicle, periodontal ligament, pulp and tooth germ, mesenchymal stem cells preferably derived from adipose, umbilical cord and bone marrow tissues; more preferably mesenchymal stem cells derived from adipose and umbilical cord, further preferably mesenchymal stem cells derived from adipose tissue. Herein cells "derived from" mean that the cells are taken from a supply source such as a tissue and grow or is manipulated in vitro. Note that, in the present invention, the mesenchymal stem cells refer to a population of mesenchymal stem cells, which may contain a plurality of types of mesenchymal stem cells different in characteristics; which may be a population of substantially the same mesenchymal stem cells; or which may be primary cells separated from a donor tissue or cells established as a cell line.

In the present invention, the mesenchymal stem cells may be derived from the same species as those of a target (subject), which are to be treated with a normal differentiation/maturation-promoting agent comprising a secretion from mesenchymal stem cells, or derived from different species. In the present invention, examples of the species of the mesenchymal stem cells include a human, a horse, a cow, a sheep, a pig, a dog, a cat, a rabbit, a mouse and a rat. The mesenchymal stem cells are preferably cells derived from the same species as the target (subject) to be treated. In the present invention, the mesenchymal stem cells may be derived from the target (subject) to be treated, more specifically, autologous cells (homologous cells) or derived from another subject belonging to the same species, more specifically, xenogeneic cells (allogeneic); and preferably, xenogeneic cells (allogeneic).

Since the mesenchymal stem cells hardly cause a rejection to allogeneic subject, it is presumed that a secretion from the mesenchymal stem cells hardly causes a rejection. Because of this, if donor cells are prepared in advance by subjecting them to expansion culture and cryopreservation, the preparation of the donor cells can be thawed at the time of need and used for preparing the secretion. The mesenchymal stem cells of the present invention are more preferably allogeneic, because it is not necessary to prepare own mesenchymal stem cells and put in use; commercialization of the cells can be easily made; and a predetermined effect can be stably and easily obtained.

In the present invention, the mesenchymal stem cells refer to any population of cells containing mesenchymal stem cells. The cell population contains at least 20% or more, preferably, 30%, 40%, 50%, 60%, 70%, 75%, 80%, 85%, 90%, 93%, 96%, 97%, 98% or 99% of mesenchymal stem cells.

In the present invention, the adipose (tissue) refers to a tissue containing mesenchymal stem cells including, e.g., adipose cells and microvascular cells; for example, a tissue obtained by surgical resection or suction of mammalian subcutaneous adipose. The adipose tissue is obtained from subcutaneous adipose. In consideration of administration to humans, human subcutaneous adipose is more preferable. An individual from which subcutaneous adipose is supplied, may be alive or dead; however, the adipose tissue to be used in the present invention is preferably taken from a living individual. When adipose is taken from an individual, liposuction such as PAL (power assist) liposuction, Elcornia laser liposuction or body jet liposuction may be mentioned. In order to maintain the state of cells, preferably an ultrasonic technique is not used.

In the present invention, umbilical cord refers to a white-tubular tissue connecting a fetus and the placenta, which is constituted of, e.g., umbilical vein, umbilical artery, glue tissue (Wharton's Jelly), and umbilical cord substrate itself, and contains a large number of mesenchymal stem cells. The umbilical cord is preferably obtained from the same species of a subject (administration target). In consideration of administration to a human, human umbilical cord is more preferable.

In the present invention, the bone marrow refers to a soft tissue filling the bone lumen, more precisely, a hematopoietic organ. The bone marrow contains bone marrow fluid. The cells present in the bone marrow fluid are referred to as bone marrow cells. The bone marrow cells include, not only e.g., red blood cells, granulocytes, megakaryocyte, lymphocytes and adipose cells, but also mesenchymal stem cells, hematopoietic stem cells and vascular endothelial precursor cells. The bone marrow cells can be taken from, for example, human iliac bone, long bone or other bones.

In the present invention, the mesenchymal stem cells derived from individual tissues, such as adipose-derived mesenchymal stem cells, umbilical cord-derived mesenchymal stem cells and bone marrow-derived mesenchymal stem cells, refer to any population of cells containing mesenchymal stem cells derived from individual tissues, such as adipose-derived mesenchymal stem cells, umbilical cord-derived mesenchymal stem cells and bone marrow-derived mesenchymal stem cells. The cell population contains at least 20% or more, preferably, 30%, 40%, 50%, 60%, 70%, 75%, 80%, 85%, 90%, 93%, 96%, 97%, 98% or 99% of tissue-derived mesenchymal stem cells such as adipose-derived mesenchymal stem cells, umbilical cord-derived mesenchymal stem cells or bone marrow-derived mesenchymal stem cells.

In the present invention, the mesenchymal stem cells may be characterized by growth properties (for example, population doubling ability, doubling time from passage to aging), karyotype analysis (for example, normal karyotype, maternal lineage or newborn lineage), surface marker expression by flow cytometry (for example, FACS analysis), immunohistochemistry and/or immunocytochemistry (for example, epitope detection), gene expression profiling (for example, gene chip array; polymerase chain reaction such as reverse transcription PCR, real time PCR, conventional PCR), miRNA expression profiling, protein array, protein secretion such as cytokine (for example, plasma coagulation analysis, ELISA, cytokine array), metabolite (metabolome analysis) and other methods known in this field.

(Method for Preparing Mesenchymal Stem Cells)

Mesenchymal stem cells can be prepared by a method known to those skilled in the art. As mentioned above, the mesenchymal stem cells may be primary cells separated from a donor tissue or cells of established cell line. Now, a method for preparing primary adipose-derived mesenchymal stem cells will be described below as an example. Adipose-derived mesenchymal stem cells may be prepared in accordance with a production method described, for example, in U.S. Pat. No. 6,777,231, for example, a method comprising the following steps (i) to (iii):

(i) a step of obtaining a cell suspension by enzymatic digestion of an adipose tissue;

(ii) a step of precipitating cells and resuspending the cells in an appropriate culture medium; and (iii) a step of culturing cells on a solid surface and removing unbound cells onto the solid surface.

The adipose tissue to be used in step (i) is preferably washed and then put in use. Cells can be washed with physiologically compatible physiological saline (for example, phosphate buffered saline (PBS)) while vigorous stirring and precipitated. This process is carried out for removing foreign substances (also referred to as debris; for example, damaged tissue, blood, red blood cells) contained in an adipose tissue. Accordingly, washing and sedimentation are generally repeated until debris is wholly removed from the supernatant. The remaining cells are present as cell clumps different in size. In order to dissociate cells while suppressing damage of cells to a minimum, the cell clumps washed are preferably treated with an enzyme for weakening or destroying binding between cells (for example, collagenase, dispase or trypsin). Although the amount of the enzyme and the treatment period thereof vary depending on the use conditions, these are known in the technical field. Cell clumps can be decomposed by other treatment (processing) methods using, e.g., mechanical stirring, ultrasonic energy and heat energy in place of or in combination with the enzymatic treatment; however, in order to suppress cell damage to a minimum, an enzyme treatment alone is preferably employed. In the case of using an enzyme, in order to suppress a harmful action to cells to a minimum, it is desirable to inactivate the enzyme by use of, e.g., culture medium, after an appropriate period.

The cell suspension obtained in step (i) contains aggregated cells like slurry or cell suspension and various contaminant cells such as red blood cells, smooth muscle cells, endothelial cells and fibroblasts. Subsequently, these contaminant cells may be separated and removed from aggregated cells. The contaminant cells, however, can be removed later in step (iii) through adhesion and washing, and thus, the separation and removal here may be skipped. Contaminant cells can be separated and removed by centrifuge, by which a cell suspension is forcibly separated into the supernatant and precipitates. The obtained precipitate containing contaminant cells is suspended in a physiologically compatible solvent. The cell suspension possibly contains red blood cells. However, the red blood cells are removed by selection by adhesion onto a solid surface as described later. Thus, a cell-lysis step is not always necessary. Red blood cells can be selectively lysed by a method known in the technical field, such as incubation in a hypertonic medium or a hypotonic medium of, for example, ammonium chloride. After the lysis, the lysate may be separated from desired cells, for example, by filtration, centrifugal sedimentation or density fraction.

In step (ii), in order to increase the purity of the mesenchymal stem cells in the cell suspension, the suspension was washed once or a plurality of times in sequential manner and centrifuged and the resultant cells may be resuspended in a culture medium. Alternatively, cells may be separated based on cell surface marker profile or size and granularity of cells.

A culture medium for use in resuspension is not particularly limited as long as mesenchymal stem cells can be cultured. The culture medium may be prepared by adding serum in basal medium and/or adding at least one serum substitute such as albumin, transferrin, fatty acid, insulin, sodium selenite, cholesterol, collagen precursor, a trace element(s), 2-mercaptoethanol and 3'-thiol glycerol. To the culture medium, if necessary, a substance such as a lipid, an amino acid, a protein, a polysaccharide, a vitamin, a growth factor, a low molecular weight compound, an antibiotic substance, an antioxidant, pyruvate, a buffer and an inorganic salt, may be further added.

Examples of the above basal medium include IMDM medium, Medium 199 medium, Eagle's Minimum Essential Medium (EMEM) medium, αMEM medium, Dulbecco's modified Eagle's Medium (DMEM) medium, Ham's F12 medium, RPMI 1640 medium, Fischer's medium, MCDB201 medium and a mixed medium of these.

Examples of the serum include, but are not limited to, human serum, fetal bovine serum (FBS), bovine serum, calf serum, goat serum, horse serum, pig serum, sheep serum, rabbit serum and rat serum. The serum may be added in basal medium in a ratio of 5 v/v % to 15 v/v % and preferably 10 v/v %.

Examples of the fatty acid include, but are not limited to, linoleic acid, oleic acid, linoleic acid, arachidonic acid, myristic acid, palmitoyl acid, palmitic acid and stearic acid. Examples of the lipid include, but are not limited to, phosphatidylserine, phosphatidyl ethanolamine and phosphatidyl choline. Examples of the amino acid include, but are not limited to, L-alanine, L-arginine, L-aspartic acid, L-asparagine, L-cysteine, L-cystine, L-glutamic acid, L-glutamine and L-glycine. Examples of the protein include, but are not limited to, ecotin, reduced glutathione, fibronectin and β2-microglobulin. Examples of the polysaccharide include, but are not limited to, glycosaminoglycan in particular such as hyaluronic acid and heparan sulfate. Examples of the growth factor include, but are not limited to, platelet-derived growth factor (PDGF), basic fibroblast growth factor (bFGF), transforming growth factor beta (TGF-β), hepatocyte growth factor (HGF), epidermal growth factor (EGF), connective tissue growth factor (CTGF) and vascular endothelial growth factor (VEGF). In order to use the adipose-derived mesenchymal stem cells obtained in the present invention for cell transplantation, a xeno-free medium containing no heterogeneous component such as serum is preferably used. Examples of the culture medium that can be used include conditioned mediums previously prepared for mesenchymal stem cells (stromal cells) by companies: PromoCell, Lonza, Biological Industries, Veritas, R&D Systems, Corning, Rohto, etc.

Subsequently, in step (iii), the cells in the cell suspension obtained in step (ii) are cultured on a solid surface using an appropriate medium as mentioned above at an appropriate cell density and culture conditions, without being differentiated. In the present invention, the "solid surface" refers to a material to which adipose tissue-derived mesenchymal stem cells can bind and adhere. In a specific embodiment, the material is a plastic material, the surface of which is treated such that binding/adhesion of mammalian cells is facilitated Although the culture vessel having a solid surface is not particularly limited in shape, e.g., a petri dish or a flask is suitably used. To remove unbound cells and cell debris, cells 30) incubated are washed.

In the present invention, the cells which finally remain bound/adhered on a solid surface can be selected as a cell population of adipose-derived mesenchymal stem cells.

The selected cells may be analyzed on the surface antigens by a conventional method using flow cytometry or the like for confirming that they are adipose-derived mesenchymal stem cells of the present invention. Additionally, the cells may be tested on the differentiation potency into each cell line, and such a differentiation can be carried out by a conventional method.

In the present invention, mesenchymal stem cells can be prepared as mentioned above. Not only primary cells but also established cells can be used. Note that, the mesenchymal stem cells can be defined as the cells, which are adhesive to plastic in the culture conditions of the standard medium, positive to surface antigens CD44, CD73 and CD90 and negative to surface antigens CD31 and CD45 and have a property of differentiating into bone cells, adipose cells and chondrocytes in the culture conditions.

(Secretion from Mesenchymal Stem Cells)

The supernatant obtained by culturing the mesenchymal stem cells as mentioned above in accordance with the following method; a fraction obtained by removing unnecessary components from the supernatant by a means such as dialysis and ultrafiltration; a fraction obtained by fractionation of the supernatant by, e.g., a column; a fraction obtained by selection with e.g., an antibody to a predetermined molecule; and a fraction and the like obtained by a centrifugal operation can be used as a secretion from mesenchymal stem cells in the normal differentiation/maturation-promoting agent of the present invention.

As the culture medium to be used for the aforementioned culture, the same mediums described in the section "Preparation of mesenchymal stem cells" can be used. As a method for culturing mesenchymal stem cells, which is not particularly limited as long as it is suitable for the type of the mesenchymal stem cell, a conventional method can be used. Culture is usually carried out in the conditions: a temperature of 30° C. to 37° C., an environment of 2% to 7% $CO_2$ and 5% to 21% $O_2$, and preferably a temperature of 37° C. and an environment of 5% $CO_2$. The timing and method for passage culture of the mesenchymal stem cells are not particularly limited as long as they are suitable for the type of the mesenchymal stem cell, and the passage culture can be carried out in the same manner as conventional one while monitoring the state of cells.

The mesenchymal stem cells cultured in the above medium are subcultured an appropriate number of times while monitoring the state of cells and thereafter cultured up to 50 to 95% confluence, preferably 60 to 90% confluence, and more preferably 70 to 80% confluence. Then, the culture medium is exchanged with a fresh culture medium. Usually, after 1 to 5 days, preferably 2 to 5 days, more preferably 2 to 4 days and further preferably 2 to 3 days, cell culture supernatant is centrifugally collected. The cell culture supernatant may be collected only once or a plurality of times over a plurality of days. The culture supernatant collected is, if necessary, subjected to filter sterilization, dialysis, concentration, column fractionation and dilution to obtain a secretion of mesenchymal stem cells which is contained in the normal differentiation/maturation-promoting agent of the present invention. Note that, the medium for passage culture may be the same or different from the medium for collecting culture supernatant.

(Method for Preparing Normal Differentiation/Maturation-Promoting Agent)

The normal differentiation/maturation-promoting agent of the present invention may contain other components as long as they do not undermine the effect of the present invention. Examples of the other components include other active ingredients and pharmaceutically acceptable components such as a carrier that general medicines and quasi drugs can contain (except the active ingredients). The secretion from mesenchymal stem cells obtained above and other components to be blended as needed, are mixed in accordance with a routine method. In this manner, the normal differentiation/maturation-promoting agent of the present invention can be prepared.

(Use of Normal Differentiation/Maturation-Promoting Agent)

The normal differentiation/maturation-promoting agent of the present invention can promote normal differentiation of stratified squamous epithelial cells such as corneal epithelial cells and also promote the formation of tight junctions between cells, thereby enhancing barrier function of a tissue. Thus, the normal differentiation/maturation-promoting agent can be used for preventing and/or treating epithelial diseases. More specifically, the normal differentiation/maturation-promoting agent of the present invention itself may be directly used for prevention and/or treatment of epithelial diseases; alternatively, a proper dosage form of the agent is prepared by adding necessary components suitable for treating each of epithelial diseases thereto, and then used as an epithelial disease therapeutic agent.

<Epithelial Disease Therapeutic Agent>

The epithelial disease therapeutic agent of the present invention is characterized in that it comprises a normal differentiation/maturation-promoting agent as mentioned above. Since the normal differentiation/maturation-promoting agent of the present invention can promote normal differentiation of stratified squamous epithelial cells such as corneal epithelial cells, and also promote formation of tight junctions between cells, thereby enhancing barrier function of the cells, the epithelial disease therapeutic agent comprising the agent produces the same effect. Note that, the detailed description of the normal differentiation/maturation-promoting agent is the same as that in the section "Agent for promoting normal differentiation/maturation of stratified squamous epithelial cells".

(Method for Preparing Epithelial Disease Therapeutic Agent)

The epithelial disease therapeutic agent of the present invention is prepared by mixing the normal differentiation/maturation-promoting agent (comprising a secretion from mesenchymal stem cells) and other components in accordance with a routine method.

(Use of Epithelial Disease Therapeutic Agent)

The epithelial disease therapeutic agent of the present invention is suitably used for preventing and/or treating diseases involving a tissue having stratified squamous epithelial cells. Of the diseases, for a disease on which an effect is produced by promoting normal differentiation of stratified squamous epithelial cells and formation of tight junction between cells, the agent is more suitably used. Examples of the stratified squamous epithelial cells include corneal epithelial cells, conjunctival epithelial cells, epidermal keratinocytes, oral epithelial cells, epiglottis epithelial cells, esophageal epithelial cells, vaginal epithelial cells, vocal cord fold epithelial cells, nasal epithelial cells and nasal vestibular epithelial cells.

Examples of a disease for which the epithelial disease therapeutic agent of the present invention is used include corneal disease, conjunctival disease, epidermal disease and oral disease. Specific examples of the disease include dry eye, pterygium, scar, EB viral keratitis, corneal epithelial stem cell deficiency, scleroderma, Sjogren's syndrome, punctate superficial keratopathy, corneal erosion, corneal ulcer, atopic dermatitis, heat corrosion, alkaline corrosion, acid corrosion, drug toxicity, Stevens-Johnson syndrome, pemphigoid, persistent corneal epithelial defect, corneal perforation, peripheral corneal ulcer, corneal ulcer, epithelial detachment after excimer laser surgery, radiation keratopathy, aniridia, corneal opacity after trachoma, Salzmann corneal degeneration, eyelid adhesion, a disease of unknown cause having corneal epithelium stem cell loss, limbal tumor, graft versus host disease (GVHD), keratitis, punctate superficial keratopathy, keratitis sicca, dry conjunctivitis, corneal dystrophy, diabetic keratopathy, corneal epithelial disorder, dry mouth (dry mouth), stomatitis, oral candidiasis, cheilitis, Plummer-Vinson syndrome, pernicious anemia (Moller-Hunter glossitis), oral lichen planus, oral candidiasis and granulomatous cheilitis. Of them, dry eye, Sjogren's syndrome, pterygium, scar, FB viral keratitis, corneal epithelial stem cell deficiency or scleroderma, for which the epithelial disease therapeutic agent of the present invention is significantly effective, is preferable and dry eye is more preferable.

Example of diseases, other than those mentioned above, to which the epithelial disease therapeutic agent of the present invention is to be applied, include, esophageal cancer, gastroesophageal reflux disease, Barrett's esophagus, pharyngeal cancer, nose cancer, vaginal cancer, anal cancer, vocal cord cancer, uveitis allergic rhinitis, systemic lupus erythematosus, chronic recurrent after, Behcet disease, Reiter disease, Crohn disease, Felty syndrome, periodic neutropenia, refractory ulcer, pemphigus, pemphigoid, herpes infection, hand-foot-and-mouth disease, herpangina, infectious mononucleosis, measles, scarlet fever, congenital or acquired epidermolysis bullosa, oral lichen planus, gingival hyperplasia, Darier disease, congenital onychomycosis, congenital dyskeratosis, and lacrimal hyposecretion.

The epithelial disease therapeutic agent of the present invention can be used in combination with another drug containing an active ingredient. The agent of the present invention may be administered simultaneously with the other drug and at an appropriate timing before or after administration of the other drug.
(Preparation of Epithelial Disease Therapeutic Agent)

The epithelial disease therapeutic agent of the present invention can be formulated into an appropriate preparation in accordance with a routine method. The dosage form of the preparation may be a solid such as a powder and a granule. In order to obtain an excellent prevention/therapeutic effect, a liquid such as a solution, an emulsion and a suspension are preferable. Particularly, if the epithelial disease therapeutic agent of the present invention is prepared as an eye drop, the dosage form is preferably a solution. As the method for producing the liquid, a method of using a secretion from mesenchymal stem cells as mentioned above as it is, a method of mixing the secretion with another solvent and a method of mixing the secretion with a suspending agent and an emulsifier can be suitably mentioned as examples. In the preparation of the epithelial disease therapeutic agent of the present invention, if necessary, an optional component such as a pharmaceutically acceptable carrier including an excipient, a binder, a solvent, a solubilizing agent, a suspending agent, an emulsifier, a tonicity agent, a buffer, a stabilizer, a soothing agent, a preservative, an antioxidant, a colorant, a lubricant, a disintegrant, a wetting agent, an adsorbent, a sweetener and a diluent, can be appropriately blended.

Although the method for administering the epithelial disease therapeutic agent of the present invention is not particularly limited, for example, administration by an eye drop, intravascular administration (preferably intravenous administration), intraperitoneal administration, enteral administration and subcutaneous administration are preferable.

The dose of the epithelial disease therapeutic agent of the present invention may vary depending on, e.g., the type of disease, the degree of the symptom, dosage form and the body weight of an administration target. The dose may be administered once a day or separated into a plurality of portions and administered in plural times. The preparation of the epithelial disease therapeutic agent of the present invention may be administered once or continuously administered. In the case of continuous administration, administration can be carried out at a frequency of once at the intervals of three days and consecutively more than twice; in particular, administration is preferably carried out at a frequency of at least once at the intervals of two days and consecutively three times or more, and more preferably at a frequency of at least once a day and consecutively four times or more.

If the epithelial disease therapeutic agent of the present invention is an eye drop, the eye drop can be prepared, if necessary, by using pharmaceutically acceptable additives in accordance with a technique ordinarily used in eye drops.

The eye drop can be prepared by, if necessary, using additives selected from tonicity agents such as sodium chloride and concentrated glycerin; pH adjuster such as hydrochloric acid and sodium hydroxide; a buffering agent such as sodium phosphate and sodium acetate; a surfactant such as polyoxyethylene sorbitan monoolcate, polyoxyl stearate 40 and polyoxyethylene hydrogenated castor oil; a stabilizer such as sodium citrate and sodium edetate; and a preservative such as benzalkonium chloride and paraben. It is sufficient if the pH of the eye drop falls within the acceptable range of ophthalmic preparations, and pH of the eye drop usually preferably falls in the range of 4 to 8.

Although an animal to be employed as an administration target for the epithelial disease therapeutic agent of the present invention is not particularly limited, a human, a monkey, a mouse, a rat, a hamster, a guinea pig, a cow, a pig, a horse, a rabbit, a sheep, a goat, a cat, a dog, etc. are preferable. Of them, a human is more preferable. The secretion of mesenchymal stem cells contained in the epithelial disease therapeutic agent of the present invention is preferably derived from cells that matches with the species of the administration-target animal, in order to more stably obtain an excellent prevention and/or therapeutic effect for a disease.
<Method for Promoting Normal Differentiation/Maturation of Stratified Squamous Epithelial Cells>

The present invention includes a method for promoting normal differentiation/maturation of stratified squamous epithelial cells characterized in that a secretion from mesenchymal stem cells is used. Normal differentiation of stratified squamous epithelial cells and formation of tight junction between cells can be promoted by adding a secretion from mesenchymal stem cells to stratified squamous epithelial cells such as corneal epithelial cells, with the result that the cells can be maturated and barrier function of a tissue can be enhanced. The detailed description of the secretion from mesenchymal stem cells and differentiation induction of stratified squamous epithelial cells is the same as that described in the section "Agent for promoting normal differentiation/maturation of stratified squamous epithelial cells". Note that, since normal differentiation and maturation are closely related events, the normal differentiation/maturation promoting method of the present invention can be referred to also as a normal differentiation promoting method.

<Method for Promoting Barrier Function of Stratified Squamous Epithelial Cells>

The present invention includes a method for promoting barrier function of stratified squamous epithelial cells, characterized in that a secretion from mesenchymal stem cells is used. Normal differentiation of stratified squamous epithelial cells and formation of tight junction between cells can be promoted by adding a secretion from mesenchymal stem cells to stratified squamous epithelial cells such as corneal epithelial cells and the cells can be maturated and barrier function of a tissue can be promoted. The detailed description of the secretion from mesenchymal stem cells and promotion of barrier function of the stratified squamous epithelial cells is the same as that described in the section "Agent for promoting normal differentiation/maturation of stratified squamous epithelial cells".

EXAMPLES

Now, the present invention will be more specifically described based on examples; however, the present invention is not limited to these examples.

1. Acquisition of Secretion from Mesenchymal Stem Cells (MSC-CM)

Adipose-derived mesenchymal stem cells (AD-MSC, PromoCell) were used as the mesenchymal stem cells and the complete synthetic medium kit for human mesenchymal stem cells (MSC-GMCD, Lonza) or growth medium DXF (PromoCell) was used as a culture fluid. AD-MSCs were seeded in the above culture fluid, at a density of 2,500-5,000 cells/cm$^2$ and cultured up to 70-80% confluence. Thereafter, the medium was exchanged with MSC-GMCD or DMEM/F-12 basal medium (Life Technologies) and culture was made for 2 to 3 days. The culture supernatant was collected and centrifuged at a rate of 300×g. The cells were removed and the supernatant was obtained for evaluation of the mesenchymal stem cell secretion (MSC-CM). The supernatant was, if necessary, sterilized through a 15 μm filter and stored at −80° C. until use.

2. Barrier Function Promotion Effect of Corneal Epithelial Cells by a Secretion from Mesenchymal Stem Cells (Measurement of Transepithelial Electrical Resistance, TER)

Human donor cornea-derived corneal epithelial cells were seeded in cell culture inserts of a 12-well plate and cultured up to confluence. As the culture fluid, DMEM/F-12 (Life Technologies) containing 2% B27supplement (Life Technologies), 20 ng/ml. KGF (Wako) and 10 μM Y-27632 (Wako) was used. After becoming fully confluent, MSC-CM was added in the inserts. As a control, a cell-free medium, which was obtained by applying the same treatment at the time of obtaining the MSC-CM, was used. TER of the corneal epithelial cells prepared was measured by use of Endohm-12 chamber and EVOM voltmeter (World Precision Instruments) with time. The results are shown in FIGS. 1 and 2.

FIG. 1 shows the results in the case of using DMEM/F-12 basal medium as culture medium for obtaining MSC-CM. As shown in FIG. 1, on and after day 5 after addition of MSC-CM, TER value of the corneal epithelial cells having MSC-CM added therein was significantly high compared to that of the control. It was found that MSC-CM has an effect to promote barrier function of the corneal epithelial cells. Particularly on and after day 7, TER value significantly increased by addition of MSC-CM. It was found that the effect of MSC-CM to promote barrier function of corneal epithelial cells is significant.

Figure 2:
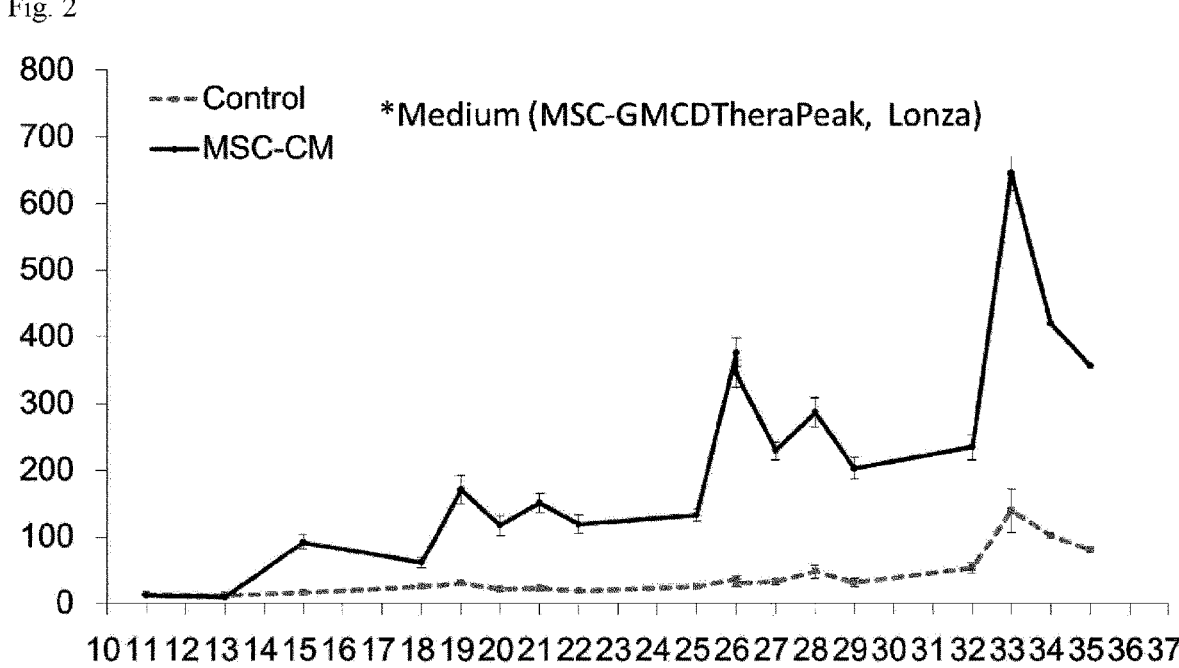
FIG. 2 is a graph showing a barrier function promotion effect of a secretion from mesenchymal stem cells (MSC-CM) on corneal epithelial cells.

FIG. 2 shows the results in the case of using MSC-GMCD as a culture medium for obtaining MSC-CM. As shown in FIG. 2, on and after day 13 after addition of MSC-CM, the TER value of corneal epithelial cells having MSC-CM added therein was significantly high compared to that of the control and increased with time, and the high value was maintained until day 33 from initiation of the culture. It was found that MSC-CM significantly promotes the barrier function of corneal epithelial cells over a long period of time and has an effect to maintain the function.

Figure 3:
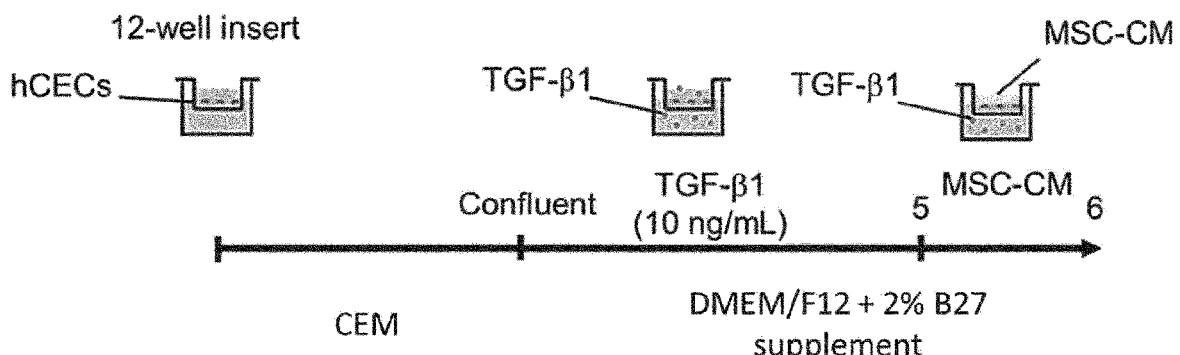
FIG. 3 shows a scheme of a test for confirming the effect of a secretion from mesenchymal stem cells (MSC-CM) on corneal epithelial cells decreased in barrier function.
Figure 4:
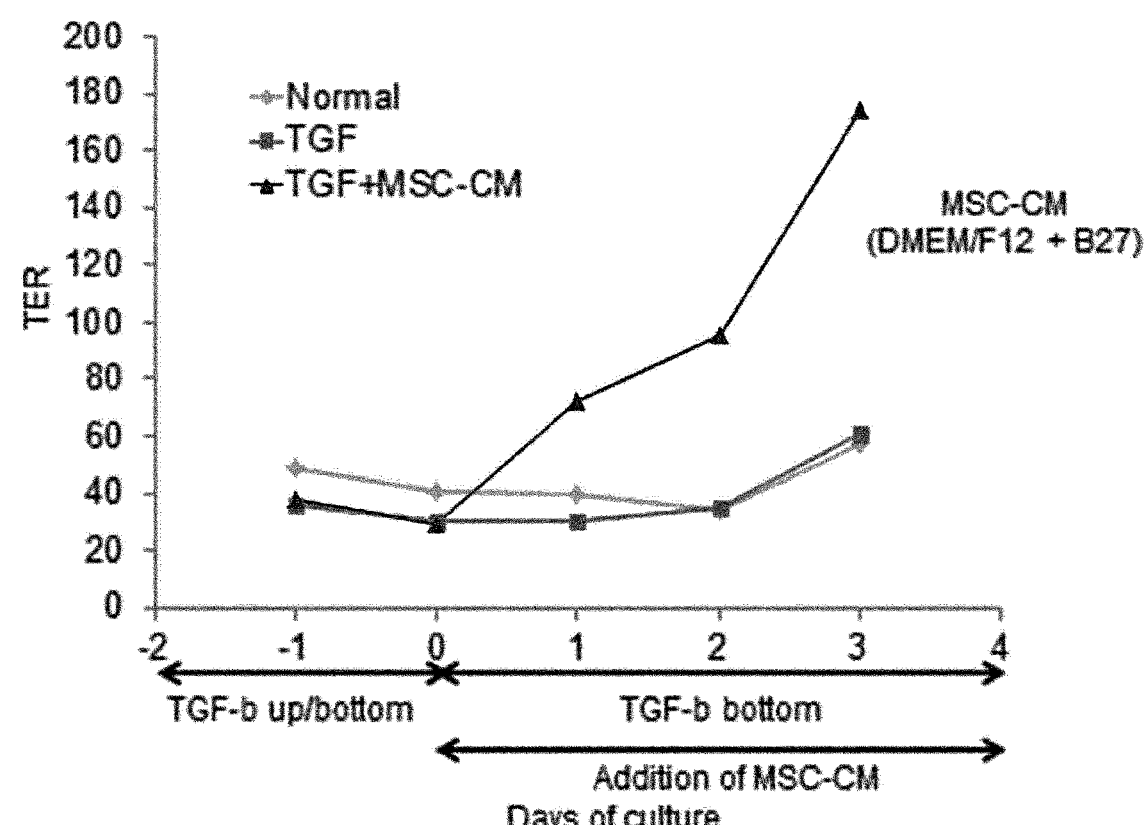
FIG. 4 is a graph showing effect of a secretion from mesenchymal stem cells (MSC-CM) on corneal epithelial cells decreased in barrier function.

Subsequently, a test was carried out for confirming the effect of MSC-CM on corneal epithelial cells, whose barrier function decreased. More specifically, human donor cornea-derived corneal epithelial cells were seeded in cell culture inserts of a 12-well plate and cultured up to confluence. After becoming fully confluent, TGF-β1 was added so as to obtain a concentration of 10 ng/ml, and culture was carried out for further 5 days. Thereafter, the culture supernatant of AD-MSC (whole MSC-GMCD medium) was added in a volume corresponding to a half of the whole medium and culture was further carried out. The scheme of the culture schedule is shown in FIG. 3. The TER value of the corneal epithelial cells prepared as mentioned above was measured with time. The results are shown in FIG. 4.

TER value of the corneal epithelial cells decreased by the treatment with TGF-β1; however, when the corneal epithelial cells were cultured in a medium containing MSC-CM, the TER value increased. The TER value returned from the decrease value by the treatment with TGF-β1 and further significantly increased. It was found that MSC-CM acts on cells decreased in barrier function and not only regains the barrier function once decreased but also further promotes the barrier function significantly.

3. Effects of Secretion from Mesenchymal Stem Cells to Promote Normal Differentiation/Maturation of Corneal Epithelial Cells and to Promote Tight Junction Formation (Gene Expression Analysis)

After the corneal epithelial cell sheets on cell culture inserts prepared in section 2 above were washed with PBS, RNA was purified by use of QIAzol Lysis Reagent (QIAGEN). Subsequently, reverse transcription was carried out by use of SuperScript (trademark) III First-Strand Synthesis SuperMix for qRT-PCR (Invitrogen). Using cDNA thus prepared as a template, quantitative real-time PCR (qRT-PCR) was carried out by ABI Prism 7500 Fast Sequence Detection System (Life Technologies). The genes subjected to expression analysis are KRT12. KRT13, KRT14, CLDN1, TJP1 and CDH1. Note that, the relative expression levels (%) of individual genes to the expression level of GAPDH regarded as 100%, are shown in FIG. 5.

Figure 5:
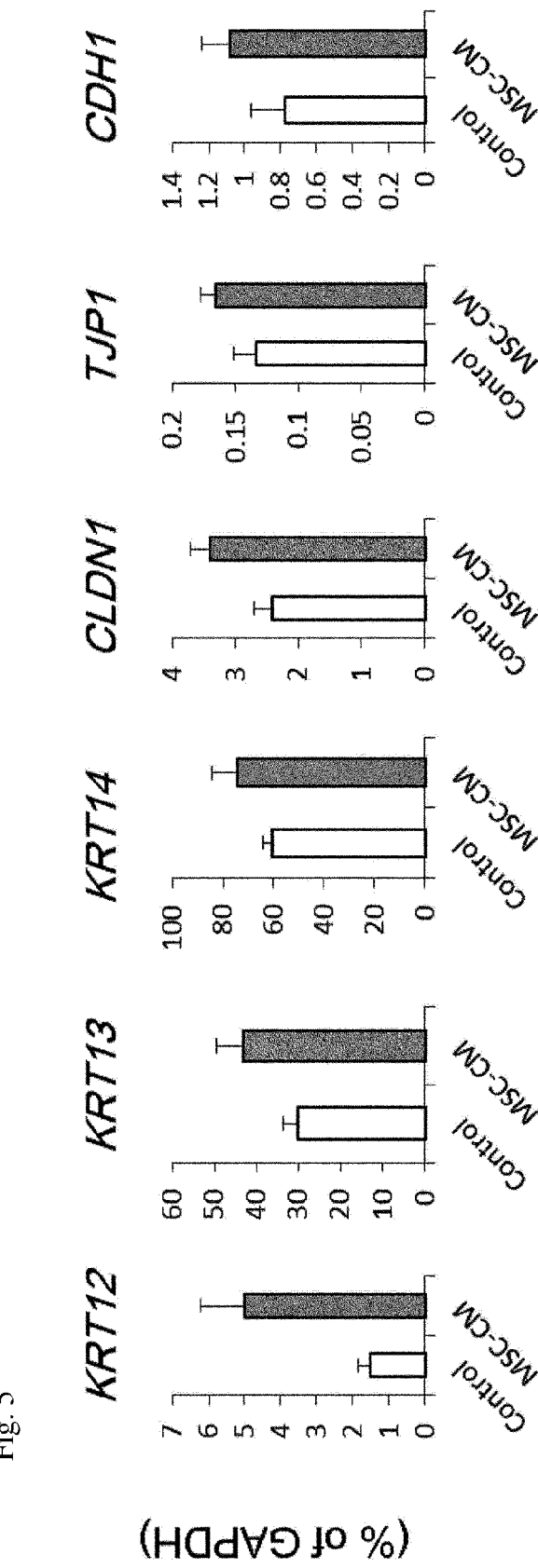
FIG. 5 shows a change in expression of various genes of corneal epithelial cells by treatment with a secretion from mesenchymal stem cells (MSC-CM).

As shown in FIG. 5, the expression levels of KRT12, KRT13, KRT14, CLDN1, TJP1 and CDH1, which are normal differentiation markers in the corneal epithelial cells, increased by adding MSC-CM. More precisely, KRT12 and KRT13 are differentiation markers of the corneal epithelial cells and conjunctival epithelial cells; KRT14 is a differentiation marker of the stratified epithelial cells; CDH1 is an epithelial cell marker; and CLDN1 and TJP1 are tight junction markers. These results show that MSC-CM promotes normal differentiation of corneal epithelial cells.

4. Effect of Secretion from Mesenchymal Stem Cells to Promote Normal Differentiation/Maturation and Formation of Tight Junction (Immunohistochemistry)

Figures 6, 7:
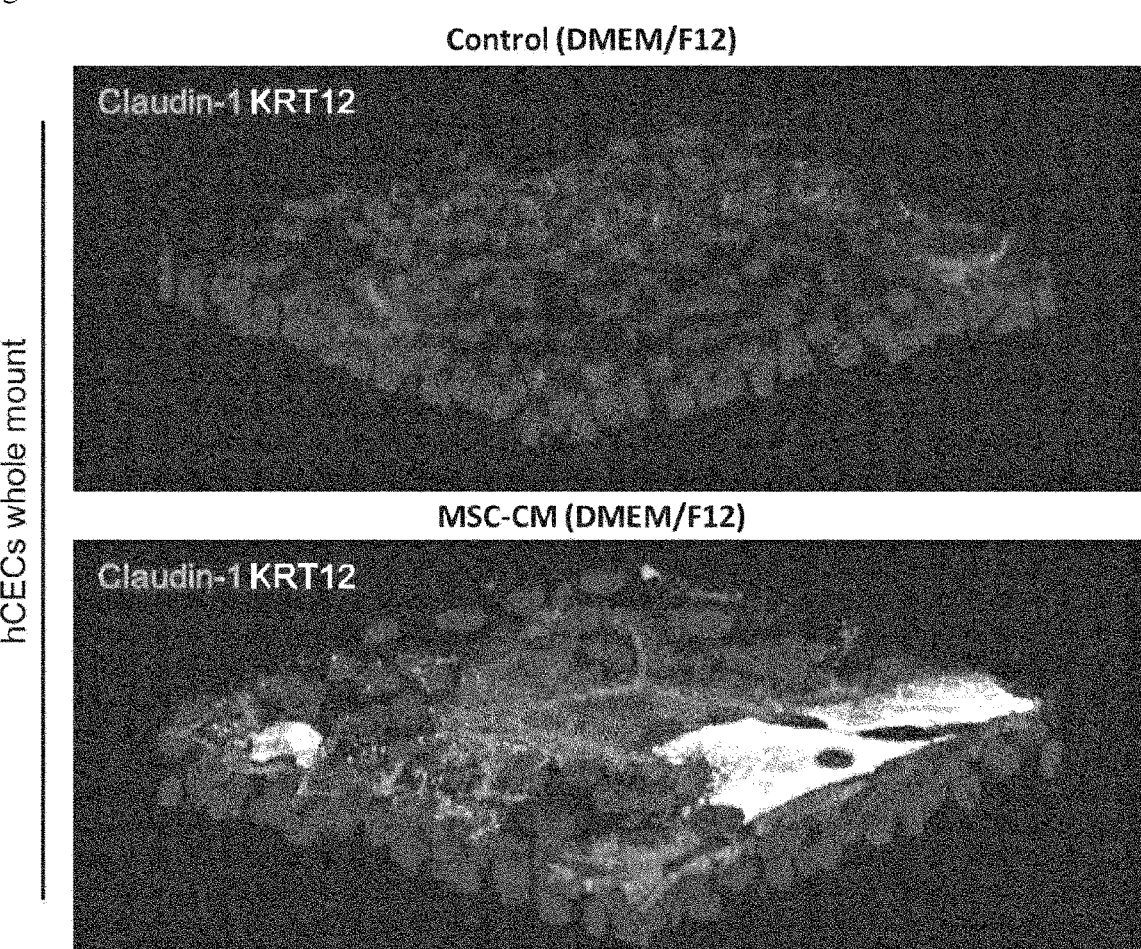
FIG. 6 immunohistochemically shows expression of Claudin-1 and KRT12 in corneal epithelial cells treated with a secretion from mesenchymal stem cells (MSC-CM).
FIG. 7 immunohistochemically shows expression of Claudin-1 and KRT12 in corneal epithelial cells treated with a secretion from mesenchymal stem cells (MSC-CM).

The corneal epithelial cells on cell culture inserts prepared in section 2 above were scooped out together with the membrane of the inserts by use of a scalpel and blocked with 5% NST (5% normal donkey serum, 0.3% Triton-X100)/TBS at room temperature for one hour. To the cells, a primary antibody was added and allowed to react at room temperature for one hour or at 4° C. overnight. After washing with TBS three times, a secondary antibody was added and allowed to react at room temperature for one hour. As the primary antibody, anti-Claudin-1 antibody (Mouse monoclonal: 2H10D10) or anti-K12 antibody (Goat polyclonal; N-16, Santa Cruz Biotechnology) was used. As the secondary antibody, Alexa Fluor (registered trademark) 488 or 567 labeled anti mouse or sheep IgG antibody (Invitrogen) was used. The antibodies each were diluted with 1% NST/TBS (1% normal donkey serum, 0.3% Triton-X100) and put in use. The nuclei were stained by treating with diluted Hoechst 33342 to 100 fold at room temperature for 10 minutes. LSM710 (Carl Zeiss) was used for observation/photographing. Using Zen software, a three-dimensional construction of a confocal image was carried out. The results are shown in FIGS. 6 and 7. In color pictures, expression of Claudin-1 (tight junction between cells) is shown in green; whereas, expression of KRT12 (flat cells normally differentiated) is shown in red As shown in FIG. 6 and FIG. 7, expression of Claudin-1 protein in the corneal epithelial cells increased by the action of MSC-CM. This fact indicates that formation of tight junction between corneal epithelial cells was promoted by the action of MSC-CM. Expression of KRT12 protein in the corneal epithelial cells also increased by the action of MSC-CM. This fact indicates that normal differentiation of the corneal epithelial cells was promoted by the action of MSC-CM. In particular, in corneal epithelial cells present at the top of multiple layers, the expressions of Claudin-1 protein and KRT12 protein significantly increased.

5. Effect of Secretion from Mesenchymal Stem Cells to Promote Normal Differentiation/Maturation and Formation of Tight Junction (Observation Under Scanning Electron Microscope)

The corneal epithelial cell sheets on cell culture inserts prepared in section 2 above were fixed with 2% glutaraldehyde, and then, washed with PBS. After dewatered with ethanol, ethanol was replaced with t-butanol. After lyophilized and sputter coated, the cell sheets were observed by a scanning electron microscope. The results are shown in FIG. 8.

Figure 8:
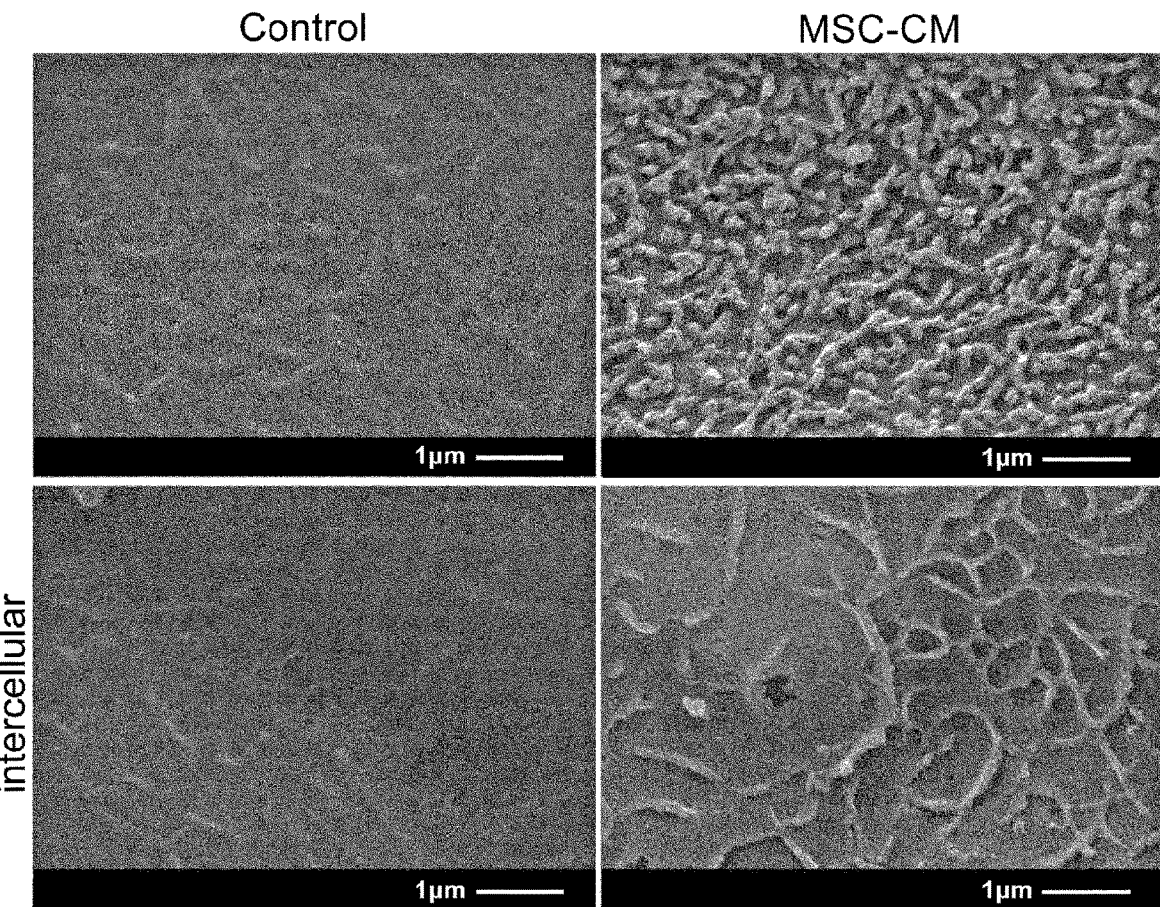
FIG. 8 shows effect to promote normal differentiation/maturation of corneal epithelial cells and an effect to promote tight junction formation by a treatment with a secretion from mesenchymal stem cells (MSC-CM) (scanning electron micrograph).

As shown in FIG. 8, maturation of microvilli on corneal epithelial cells was significantly induced by the action of MSC-CM, with the result that corneal epithelial cells were normally differentiated; at the same time, formation of tight junction between cells was promoted.

6. Effect of Secretion from Mesenchymal Stem Cells to Promote Normal Differentiation/Maturation and Formation of Tight Junction (RNA-Sequence Analysis)

The human corneal epithelial cells, to which MSC culture supernatant (CM) was added, were cultured for 16 hours in accordance with the method described in section 2 above. The human corneal epithelial cells obtained were collected by QIAzol Reagent and RNA was purified by use of miRNeasy Mini Kit (Qiagen) in accordance with a recommended method. A library was prepared by TruSeq strand mRNA sample prep kit (Illumina, San Diege, CA). RNA was sequenced by Illumina Hiseq 2500. Using Illumina Casava ver1.8.2 software, base call was carried out. Based on the human reference genome (hg19), mapping was carried out by use of TopHat (ver. 2.0.13), Bowtie2 (ver. 2.2.3) and SAMtools (ver. 0.1.19.). Using Cuffnom (ver. 2.3.1), FPKM (the number of fragments per kilobase of exon per million mapped fragments) values were calculated. Analysis results are shown in Table 1.

TABLE 1

| FPKM | Control | CM |
|---|---|---|
| MUC1 | 0.205 | 5.960 |
| MUC15 | 0.881 | 2.384 |
| MUC16 | 4.288 | 19.101 |
| MUC20 | 3.705 | 10.857 |
| MUC21 | 1.686 | 9.406 |
| MUC22 | 11.175 | 46.277 |
| MUC4 | 0.209 | 2.715 |
| MUCH | 0.401 | 0.653 |
| CLDN1 | 172.199 | 276.781 |
| CLDN11 | 0.855 | 0.651 |
| CLDN12 | 5.884 | 11.250 |
| CLDN15 | 1.680 | 1.880 |
| CLDN16 | 0.446 | 0.533 |
| CLDN23 | 0.452 | 1.856 |
| CLDN4 | 77.083 | 525.564 |
| CLDN7 | 67.374 | 205.666 |
| TJP1 | 22.882 | 45.369 |
| TJP2 | 54.760 | 112.420 |
| TJP3 | 2.177 | 4.908 |

As shown in Table 1, MUC gene group involved in maturation of the cornea and CLDN and TJP gene groups involved in formation of tight junction were increased in expression by addition of the MSC culture supernatant (CM).

7. Therapeutic Effect of MSC Secretion on Dry Eye Model Animal

Figure 9:
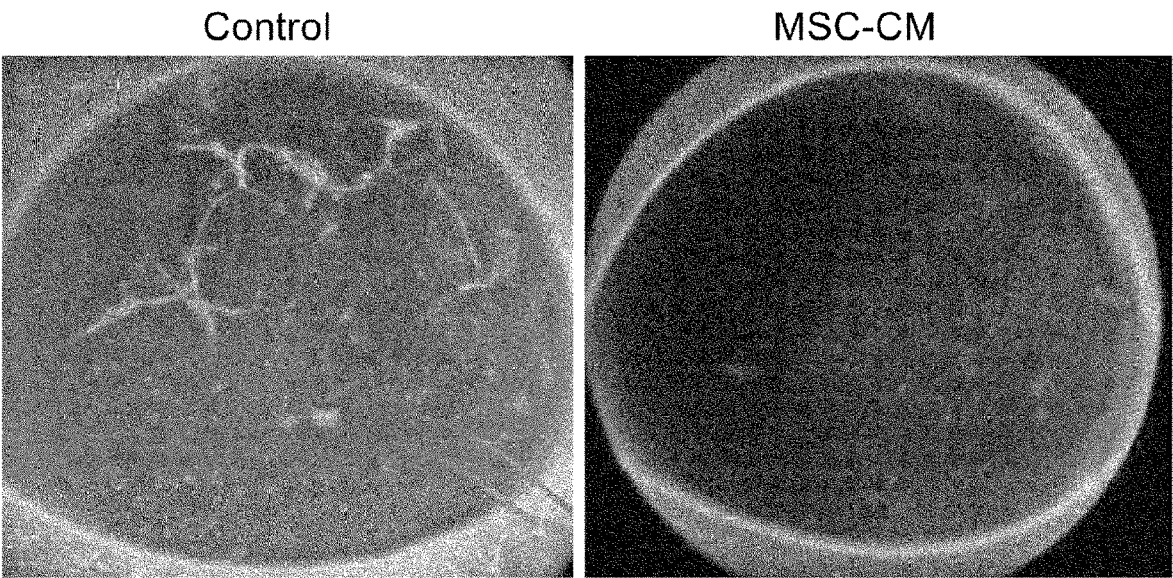
FIG. 9 shows a therapeutic effect of a secretion from mesenchymal stem cells (MSC-CM) on dry-eye model animal.

A dry eye model was prepared based on Fujihara et al. method (Improvement of corneal barrier function by the P2Y (2) agonist INS365 in a rat dry eye model. Invest Ophthalmol Vis Sci. 2001 January; 42 (1): 96-100) by excising the extraorbital lacrimal gland from one of the eyes of SD rat (male). The dry eye model rat was anesthetized and the skin was dissected, and then, the extraorbital lacrimal gland was excised out. After lacrimal gland was removed, instillation of an eye drop containing mesenchymal stem cell secretion (culture supernatant) was continued for 4 weeks. When the ocular surface was analyzed, the rat was anesthetized and staining was made with fluorescein to evaluate a corneal epithelial disorder. The results are shown in FIG. 9. The right photograph in FIG. 9 shows an eyeball to which eye drop containing MSC secretion was instilled; whereas, the left photograph shows the control.

As shown in FIG. 9, the symptom of dry eye was significantly improved by instillation of the eye drop containing MSC secretion. As described, MSC secretion has an excellent therapeutic effect on dry eye.

INDUSTRIAL APPLICABILITY

According to the present invention, normal differentiation/maturation and formation of tight junction between cells can be promoted, thereby enhancing barrier function, by adding a normal differentiation/maturation-promoting agent comprising a secretion from mesenchymal stem cells to stratified squamous epithelial cells, e.g., corneal epithelial cells. The therapeutic agent comprising the normal differentiation/maturation-promoting agent is effective for a disease of a tissue having stratified squamous epithelial cells, for example, an epithelial disease such as dry eye.

The invention claimed is:

1. A method for promoting normal differentiation or maturation of stratified squamous epithelial cells, comprising administering an effective amount of a culture supernatant of adipose-derived mesenchymal stem cells to a subject in need thereof, wherein the culture supernatant does not include animal serum and wherein administration of the culture supernatant results in increased expression of KRT12 in the epithelial cells.

2. The method for promoting normal differentiation or maturation of stratified squamous epithelial cells according to claim 1, wherein the stratified squamous epithelial cells comprise at least one type of cells selected from the group consisting of corneal epithelial cells, conjunctival epithelial cells, epidermal keratinocytes, oral epithelial cells, epiglottis epithelial cells, esophageal epithelial cells, vaginal epithelial cells, vocal cord fold epithelial cells, nasal epithelial cells, and nasal vestibular epithelial cells.

3. A method for treating an epithelial disease involving a tissue having stratified squamous epithelial cells, comprising administering an effective amount of a culture supernatant of mesenchymal stem cells to a subject in need thereof, wherein, the culture supernatant does not include animal serum;

the mesenchymal stem cells are adipose-derived mesenchymal stem cells;

administration of the culture supernatant results in an increased expression of KRT12 in the epithelial cells; and the stratified squamous epithelial cells comprise at least one type of cells selected from the group consisting of corneal epithelial cells, conjunctival epithelial cells, epidermal keratinocytes, oral epithelial cells, epiglottis epithelial cells, esophageal epithelial cells, vaginal epithelial cells, vocal cord fold epithelial cells, nasal epithelial cells, and nasal vestibular epithelial cells.

4. The method for treating an epithelial disease involving a tissue having the stratified squamous epithelial cells according to claim 3, wherein the epithelial disease is a corneal disease, a conjunctival disease, an oral disease, or an epidermal disease.

5. The method for treating an epithelial disease involving a tissue having the stratified squamous epithelial cells according to claim 4, wherein the epithelial disease is dry eye, pterygium, scar, EB viral keratitis, corneal epithelial stem cell deficiency, Sjogren's syndrome, or scleroderma.

* * * * *